United States Patent [19]

Ricigliano et al.

[11] Patent Number: 5,795,872
[45] Date of Patent: Aug. 18, 1998

[54] DNA CONSTRUCT FOR IMMUNIZATION

[75] Inventors: Joseph W. Ricigliano; Barbara A. Araneo, both of Salt Lake City, Utah

[73] Assignee: Pharmadigm, Inc., Salt Lake City, Utah

[21] Appl. No.: 530,529

[22] Filed: Sep. 19, 1995

[51] Int. Cl.$^6$ .................. A61K 45/00; A61K 45/05; C12N 15/11; C12N 15/63
[52] U.S. Cl. .................. 514/44; 435/320.1; 536/23.1; 536/23.7; 536/23.72; 536/24.1
[58] Field of Search .................. 435/320.1; 514/44; 536/23.1, 23.7, 23.72, 24.1

[56] References Cited

U.S. PATENT DOCUMENTS

| | | | |
|---|---|---|---|
| 5,169,763 | 12/1992 | Kieny et al. | 435/69.3 |
| 5,252,479 | 10/1993 | Srivastava | 435/235.1 |
| 5,266,488 | 11/1993 | Ordahl et al. | 439/69.1 X |
| 5,273,876 | 12/1993 | Hock et al. | 435/235.1 |
| 5,352,595 | 10/1994 | Tapscott et al. | 435/172.3 |
| 5,374,544 | 12/1994 | Schwartz et al. | 435/172.3 |

FOREIGN PATENT DOCUMENTS

| | | |
|---|---|---|
| 1319629 | 6/1993 | Canada . |
| 0 351 921 | 1/1990 | European Pat. Off. . |
| WO 93/09236 | 5/1993 | WIPO . |
| WO 94/11505 | 5/1994 | WIPO . |
| WO 94/28151 | 12/1994 | WIPO . |

OTHER PUBLICATIONS

Chang, P.-Y. et al. (1994). "Expression of a Dominant-negative Mutant Human Insulin Receptor in the Muscle of Transgenic Mice." *J. Biol. Chem.* 269:16034–16040.
Lee, C. et al. (1993). "Mdx Transgenic Mouse: Restoration of Recombinant Dystrophin to the Dystrophic Muscle." *Hum. Gene Therapy* 4;273–281.
Tsika R. et al. (1995). "M–creatine kinase gene expression in mechanically overloaded skeletal muscle of transgenic mice." *Am. J. Physiol.* 269:3 Pt. 1:C665–C674.
Vincent, C.K., et al. (1993). "Different Regulatory Sequences Control Creatine Kinase–M Gene Expression in Directly Injected and Cardiac Muscle." *Mol. Cell. Biol.* 13:1264–1272.
Svensson, E.C. et al. (1996). "Muscle–based gene therapy: realistic possibilities for the future." *Mol. Med. Today* Apr. 1996:166–172.
Kriesel, J.D. et al. (1995). "Nucleic Acid Vaccine Against Herpes Simplex Type 2 (HSV–2): Use of a Muscle–Specific Promoter and the HSV–2 Glycoprotein D (gD2) Gene." *Abstracts of the 35th Interscience Conference on Antimicrobial Agents and Chemotherapy*, p. 199.
Kriesel, J.D. et al. (1995). "Vitamin D3 as an Adjuvant with a Nucleic Acid Vaccine Against Herpes Simplex Type 2." *Abstracts of the 35th Interscience Conference on Antimicrobial Agents and Chemotherapy*, p. 199.
Jaynes, J.B. et al. (1986). *Mol. Cell. Biol.* 6:8 (2855–2864).
Jaynes, J.B. et al. (1988). *Mol. Cell. Biol.* 8:1 (62–70).
Sternberg, E.A. et al. (1988). *Mol. Cell. Biol.* 8:7 (2896–2909).
Johnson, J.E. et al. (1989). *Develop. Biol.* 134:258–262.
Johnson, J.E. et al. (1989). *Mol. Cell. Biol.* 9:8 (3393–3399).
Muggridge, M. (1990). *J. Virol.* 64:8 (3617–3626).
Wolff, J.A. et al. (1990). *Science* 247:1465–1468.
Olson, E.N. (1990). *Genes & Develop.* 4:1454–1461.
Kitsis, R.N. et al. (1991). *Proc. Natl. Acad. Sci. USA* 88:4138–4142.
Donoghue, M.J. et al. (1992). *Cell* 69:67–77.
Grieshammer, U. et al. (1992). *Cell* 69:79–93.
Hart, S. (1992). *Bioscience* 42:8 (582–586).
Takeda, S. et al. (1992). *J. Biol. Chem.* 267:24 (16957–16967).
Giallongo, A. et al. (1993). *Eur. J. Biochem.* 214:367–374.
Prigozy, T. et al. (1993). *Somatic Cell Mol. Genets.* 29:2 (111–122).
Ulmer, J.B. et al. (1993). *Science* 259:1745–1749.
von Harsdorf, R. et al. (1993). *Circul. Reg.* 72:689–695.
Wang, B. et al. (1993). *Proc. Natl. Acad. Sci. USA* 90:4156–4160.
Yankauckas, M.A. (1993). *DNA Cell Biol.* 12:9 (771–776).
Bichko, V. et al. (1994) *J. Virol.* 68:8 (5247–5252).
Fuzio, V.M. et al. (1994). *Biochem. Biophys. Res. Comm's.* 200:1 (298–305).
Flotte, T.R. et al. (1994). *Am. J.Resp. Cell Mol. Biol.* 11:517–524.
Hawkins, R.E. et al. (1994). *Blood* 83:11 (3279–3288).
Katsumi, A. et al. (1994). *Human Gene Therapy* 5:1335–1339.
Raz, E. et al. (1994). *Proc. Natl. Acad. Sci. USA* 91:9519–9523.

(List continued on next page.)

*Primary Examiner*—Johnny Railey
*Attorney, Agent, or Firm*—Rothwell, Figg, Ernst & Kurz, P.C.

[57] ABSTRACT

The present invention is directed to a DNA construct which is useful for immunization or gene therapy. The construct of the invention comprises muscle specific regulatory elements, such as a promoter or a promoter and one or more enhancer elements, and a DNA sequence under control of the muscle specific regulatory elements. Several DNA sequences may be incorporated into the DNA construct. In one embodiment, the DNA sequence codes for an antigen, antigenic determinant or an epitope of an antigen. In a second embodiment, the DNA sequence is a normal muscle gene which is effected in a muscle disease. In a third embodiment, the DNA sequence is an antisense for blocking an abnormal muscle gene. In a fourth embodiment, the DNA sequence codes for a protein which circulates in the mammalian blood or lymphatic systems. The present invention is useful for ameliorating the effects of diseases of muscle by expression of the normal gene or blocking abnormal gene expression within muscle cells, for the heterologous expression of a transgene which codes for a circulating protein or a protein which modifies a disease state in which muscle is not primarily involved and for vaccine development.

16 Claims, 7 Drawing Sheets

OTHER PUBLICATIONS

Vile, R.G. et al. (1994). *Ann. Oncol.* 5(Supp. 4):S59–S65.

Johanning, F.W. et al. (1995). *Nucl. Acids Res.* 2:9 (1495–1501).

March, K.L. et al. (1995). *Hum. Gene Ther.* 6:41–53.

Qin, L. et al. (1995). *Transplant* 59:809–816.

Wang, C. et al. (1995). *J.Clin. Invest.* 95:1710–1716.

Wilkinson, G.W.G. et al. (1995). *Brit. Med. Bull.* 51:1 (205–216).

Marshall, E. (1995). *Science* 269:1050–1055.

-1354

CAGCTGAGGT GCAAAAGGCT CCTGTCATAT TGTGTCCTGC TCTGGTCTGC CTTCACAGCT

TGGGGGCCAC CTAGCCCACC TCTCCCTAGG GATGAGAGCA GCCACTATGG GTCTAGGCTG

CCCATGTAAG GAGGCAAGGC CTGGGGACAC CCGAGATGCC TGGTTATAAT TAACCCAGAC

ATGTGGCTGC TCCCCCCCCC CAACACCTGC TGCCTGAGCC TCACCCCCAC CCCGGTGCCT

GGGTCTTAGG CTCTGTACAC CATGGAGGAG AAGCTCGCTC TAAAAATAAC CCTGTCCCTG

GTGGATCCNN TCCGGAGGGG CAGGCTGAGG GCGGCCACTT CCCTCAGCCG CAGTTTGTTT

TCCCAAGAAT GGTTTTTCTG CTTCTGTAGC TTTTCCTGTC AATTCTGCCA TGGTGGAGCA

GCCTGCACTG GGCTTCTGGG AGAAACCAAA CCGGGTTCTA ACCTTTCAGC TACAGTCATT

GCCTTTCCTG TAGATGGGCG ACTACAGCCC CACCCCCACC CCCGTCTCCT GTATCCTTCC

TGGGCCTGGG GATCCTAGGC TTTCACTGGA AATTTCCCCC CAGGTGCTGT AGGCTAGAGT

CACGGCTCCC AAGAACAGTG CTTGCCTGGC ATGCATGGTT CTGAACCTCC AACTGCAAAA

AATGACACAT ACCTTGACCC TTGGAAGGCT GAGGCAGGGG GATTGCCATG AGTGCAAAGC

CAGACTGGGT GGCATAGTTA GACCCTGTCT CAAAAAACCA AAAACAATTA ATAACTAAA

GTCAGGCAAG TAATCCTACT CAGGAGACTG AGGCAGAGGG ATTGTTACAT GTCTGAGGCC

AGCCTGGACT ACATAGGGTT TCAGGCTAGC CCTGTCTACA GAGTAAGGCC CTATTTCAAA

AACACAAACA AAATGGTTCT CCCAGCTGCT AATGCTCACC AGGCAATGAA GCCTGGTGAG

CATTAGCAAT GAAGGCAATG AAGGAGGGTG CTGGCTACAT CAGGCTGTGG GGGACTGAGG

GCAGGCTGTA ACAGGCTTGG GGGCCAGGGC TTATACGTGC CTGGGACTCC CAAAGTATTA

CTGTTCCATG TTCCCGGCGA AGGGCCAGCT GTCCCCGCC AGCTAGACTC AGCACTTAGT

TTAGGAACCA GTGAGCAAGT CAGCCCTTGG GGCAGCCCAT ACAAGGCCAT GGGGCTGGGC

AAGCTGCACG CCTGGGTCCG GGGTGGGCAC GGTGCCCGGG CAACGAGCTG AAAGCTCATC

TGCTCTCAGG GGCCCCTCCC TGGGACAGC CCCTCCTGGC TAGTCACACC CTGTAGGCTC

+7
CTCTATATAA CCCAGGGGCA CAGGGCTGC CCCCGGGTCA C

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1361 base pairs
        ( B ) TYPE: nucleic acid
        ( C ) STRANDEDNESS: double
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Mouse     ( i x ) FEATURE:
        ( A ) NAME/KEY: misc_feature
        ( B ) LOCATION: 1..1354
        ( D ) OTHER INFORMATION: /note= "5'nontranscribed sequence"

( i x ) FEATURE:
        ( A ) NAME/KEY: 5'UTR
        ( B ) LOCATION: 1355..1361

( x i ) SEQUENCE DESCRIPTION: SEQ ID NO:1:

```
CAGCTGAGGT  GCAAAAGGCT  CCTGTCATAT  TGTGTCCTGC  TCTGGTCTGC  CTTCACAGCT        60

TGGGGGCCAC  CTAGCCCACC  TCTCCCTAGG  GATGAGAGCA  GCCACTATGG  GTCTAGGCTG       120

CCCATGTAAG  GAGGCAAGGC  CTGGGGACAC  CCGAGATGCC  TGGTTATAAT  TAACCCAGAC       180

ATGTGGCTGC  TCCCCCCCCC  CAACACCTGC  TGCCTGAGCC  TCACCCCAC   CCCGGTGCCT       240
```

-continued

```
GGGTCTTAGG CTCTGTACAC CATGGAGGAG AAGCTCGCTC TAAAAATAAC CCTGTCCCTG    300
GTGGATCCNN TCCGGAGGGG CAGGCTGAGG GCGGCCACTT CCCTCAGCCG CAGTTTGTTT    360
TCCCAAGAAT GGTTTTTCTG CTTCTGTAGC TTTTCCTGTC AATTCTGCCA TGGTGGAGCA    420
GCCTGCACTG GGCTTCTGGG AGAAACCAAA CCGGGTTCTA ACCTTTCAGC TACAGTCATT    480
GCCTTTCCTG TAGATGGGCG ACTACAGCCC CACCCCCACC CCCGTCTCCT GTATCCTTCC    540
TGGGCCTGGG GATCCTAGGC TTTCACTGGA AATTTCCCCC CAGGTGCTGT AGGCTAGAGT    600
CACGGCTCCC AAGAACAGTG CTTGCCTGGC ATGCATGGTT CTGAACCTCC AACTGCAAAA    660
AATGACACAT ACCTTGACCC TTGGAAGGCT GAGGCAGGGG GATTGCCATG AGTGCAAAGC    720
CAGACTGGGT GGCATAGTTA GACCCTGTCT CAAAAAACCA AAAACAATTA AATAACTAAA    780
GTCAGGCAAG TAATCCTACT CAGGAGACTG AGGCAGAGGG ATTGTTACAT GTCTGAGGCC    840
AGCCTGGACT ACATAGGGTT TCAGGCTAGC CCTGTCTACA GAGTAAGGCC CTATTTCAAA    900
AACACAAACA AAATGGTTCT CCCAGCTGCT AATGCTCACC AGGCAATGAA GCCTGGTGAG    960
CATTAGCAAT GAAGGCAATG AAGGAGGGTG CTGGCTACAT CAGGCTGTGG GGGACTGAGG   1020
GCAGGCTGTA ACAGGCTTGG GGGCCAGGGC TTATACGTGC CTGGGACTCC CAAAGTATTA   1080
CTGTTCCATG TTCCCGGCGA AGGGCCAGCT GTCCCCCGCC AGCTAGACTC AGCACTTAGT   1140
TTAGGAACCA GTGAGCAAGT CAGCCCTTGG GGCAGCCCAT ACAAGGCCAT GGGGCTGGGC   1200
AAGCTGCACG CCTGGGTCCG GGGTGGGCAC GGTGCCCGGG CAACGAGCTG AAAGCTCATC   1260
TGCTCTCAGG GGCCCCTCCC TGGGGACAGC CCCTCCTGGC TAGTCACACC CTGTAGGCTC   1320
CTCTATATAA CCCAGGGGCA CAGGGCTGC CCCCGGGTCA C                        1361
```

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "Synthetic primer"

( i i i ) HYPOTHETICAL: NO

( x i ) SEQUENCE DESCRIPTION: SEQ ID NO:2:

```
GAAGATCTCA GCTGAGGTGC AAAAGGCTCC TG                                   32
```

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "Synthetic primer"

( i i i ) HYPOTHETICAL: NO

( x i ) SEQUENCE DESCRIPTION: SEQ ID NO:3:

```
CCCAAGCTTG TGACCCGGGG GCAGCCCTG TGCC                                 34
```

DNA CONSTRUCT FOR IMMUNIZATION

BACKGROUND OF THE INVENTION

The present invention is directed to a DNA construct which can be used for either direct or indirect gene therapy. The DNA construct contains muscle specific regulatory elements and a DNA sequence which encodes an antigen for immunization or a protein for gene therapy or the DNA sequence is an antisense sequence for gene therapy.

The publications and other materials used herein to illuminate the background of the invention, and in particular, cases to provide additional details respecting the practice, are incorporated herein by reference, and for convenience, are referenced by author and date in the following text and respectively grouped in the appended List of References.

Initial efforts toward postnatal gene therapy have relied on indirect means of introducing new genetic information into tissues: target cells are removed from the body, infected with viral vectors carrying the new genetic information and then replanted into the body. (Ledley, 1987; Eglitis and Anderson, 1988; Friedmann, 1989). However, indirect gene transfer is not useful for many applications of gene therapy. In these instances, direct introduction of genes into tissues in vivo is desired.

Several gene transfer systems have been developed to directly or indirectly introduce genes into tissues in vivo. These systems include viral and nonviral transfer methods. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990; Srivastava, 1993), herpesviruses including HSV and EBV (Margolskee, 1992; Johnson et al., 1992; Fink et al., 1992; Breakfield and Geller, 1987; Freese et al., 1990), and retroviruses of avian (Brandyopadhyay and Temin, 1984; Petropoulos et al., 1992), murine (Miller, 1992; Miller et al., 1985; Sorge et al, 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al, 1980; Brinster et al., 1981; Constantini and Lacy, 1981); membrane fusion-mediated transfer via liposomes (Felgner et al., 1987; Wang and Huang, 1989; Kaneda et al, 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989b; Wolff et al., 1991; Wagner et al., 1990; Wagner et al., 1991; Cotten et al., 1990; Curiel et al., 1991a; Curiel et al., 1991b). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Direct gene transfer into mammalian somatic tissues in vivo is a developing technology with potential applications in human gene therapy. The principal advantages of such an approach are the simplicity and safety of the techniques. Three types of direct gene transfer methodology have been developed: particle bombardment, liposome-mediated deliver and naked DNA transfer. In particle bombardment methods, first applied to the transformation of plant tissue (Klein et al., 1987), the DNA-coated particles are accelerated to high velocity so that they are able to penetrate target organs, tissues or single cells efficiently. Gene transfer to various mammalian somatic tissue has been effectively achieve in vito, ex vivo and in vitro with particle bombardment (Yang et al., 1990). Liposome-mediated gene transfer is also an effective method for in vivo gene transfer. For example, DNA-liposome complexes have been used for direct gene transfer to human melanoma cells (Nabel et al., 1993).

A challenge to the development of vaccines against viruses such as influenza A or human immunodeficiency virus (HIV), against which neutralizing antibodies are generated, is the diversity of the viral envelope proteins among different isolates or strains. Because CTLs in both mice and humans are capable of recognizing epitopes derived from conserved internal viral proteins (Townsend et al., 1989) and are thought to be important in the immune response against viruses (Taylor et al. 1986), efforts have been directed toward the development of CTL vaccines capable of providing heterologous protection against different viral strains. $CD8^+$ CTLs kill virally infected cells when their T cell receptors recognize viral peptides associated with major histocompatibility complex (MHC) class I molecules (Germain, 1981). These peptides are derived from endogenously synthesized viral proteins, regardless of the protein's location or function in the virus. Thus, by recognition of epitopes from conserved viral proteins, CTLs may provide cross-strain protection. Peptides capable of associating with MHC class I molecules for CTL recognition originate from proteins that are present in or pass through the cytoplasm or endoplasmic reticulum (Yewdell et al. 1989). Therefore, in general, exogenous proteins, which enter the endosomal processing pathway (as in the case of antigens presented by MHC class II molecules), are not effective at generating $CD8^+$ CTL responses.

Most efforts to generate CTL responses have either used replicating vectors to produce the protein antigen in the cell (Hahn et al. 1992) or have focused on the introduction of peptides into the cytosol (Collins et al. 1992). Both of these approaches have limitations that may reduce their usefulness as vaccines. Retroviral vectors have restrictions on the site and structure of polypeptides that can be expressed as fusion proteins and still maintain the ability of the recombinant virus to replicate (Miller et al. 1992), and the effectiveness of vectors such as vaccinia for subsequent immunizations may be compromised by immune responses against the vectors themselves (Cooney et al. 1991). Also, viral vectors and modified pathogens have inherent risks that may hinder their use in humans (Mascola et al. 1989). Furthermore, the selection of peptide epitopes to be presented is dependent on the structure of an individual's MHC antigens, and peptide vaccines may therefore have limited effectiveness due to the diversity of MHC haplotypes in outbred populations (Townsend et al. 1989; Taylor et al. 1986; Germain. 1981). Hence, immunization with nonreplicating plasmid DNA encoding viral proteins may be advantageous because no infectious agent is involved, no assembly of virus particles is required, and determinant selection is permitted. Because the sequence of nucleoprotein (NP) is conserved among various strains of influenza (Gammelin et al. 1989; Gorman et al. 1991), protection was achieved here against subsequent challenge by a virulent strain of influenza A that was heterologous to the strain from which the gene for NP was cloned. Vectors used vaccines have also been described by Kieny et al. (1992), Hock et al. (1993) and Yankaukas et al. (1993).

Intramuscular (i.m.) injection of DNA expression vectors in mice has been demonstrated to result in the uptake of DNA by the muscle cells and expression of the protein encoded by the DNA (Ascadi et al. 1991; Fazio et al., 1994). Plasmids were shown to be maintained episomally and did not replicate. Subsequently, persistent expression was observed after i.m. injection in skeletal muscle of rats, fish and primates, and in cardiac muscle of rats (Wolff et al. 1992).

Muscle creatine kinase (MCK) is expressed at high levels in both skeletal and cardiac muscle of adult animals (Eppenberger et al. 1964; Jockers-Wretou et al. 1975; Richterich et al. 1967; Tanzer et al. 1959). Activation of MCK transcription during skeletal myoblast differentiation has been shown (Chamberlain et al. 1985; Jaynes et al. 1986; Perriard 1979; Perriard et al. 1978; Rosenberg et al. 1982), and multiple cis-acting regulatory sequences have been identified in the 5' flanking sequence and first intron of the MCK gene (Jaynes et al. 1988; Sternberg et al. 1988). The best-characterized element is a 207-base-pair (bp) muscle-specific enhancer located about 1,100 nucleotides (nt) 5' of the MCK transcription start site. Another enhancer element is located within a 900-nt region in the first intron. The proximal 776-nt 5' MCK sequence also displays muscle cell type specificity in cultured cells, but the absolute level of expression from this element is quite low compared with expression when either enhancer is present (Jaynes et al. 1988). A myocyte-specific binding activity, MEF1, that interacts with both enhancers but not the proximal element, has been identified (Buskin et al. 1989). Furthermore, the intact MEF1 site is required for the 5' enhancer to function in MCK expression during skeletal myoblast differentiation in culture.

SUMMARY OF THE INVENTION

The present invention is directed to a DNA construct which is useful for immunization or gene therapy. The construct of the invention comprises muscle specific regulatory elements, such as a promoter or a promoter and one or more enhancer elements, and a DNA sequence under control of the muscle specific regulatory elements. Several DNA sequences may be incorporated into the DNA construct. In one embodiment, the DNA sequence codes for an antigen, antigenic determinant or an epitope of an antigen. In a second embodiment, the DNA sequence is a normal muscle gene which is effected in a muscle disease. In a third embodiment, the DNA sequence is an antisense for blocking an abnormal muscle gene. In a fourth embodiment, the DNA sequence codes for a protein which circulates in the mammalian blood or lymphatic systems. The present invention is useful for ameliorating the effects of diseases of muscle by expression of the normal gene or blocking abnormal gene expression within muscle cells, for the heterologous expression of a transgene which codes for a circulating protein or a protein which modifies a disease state in which muscle is not primarily involved and for vaccine development.

BRIEF DESCRIPTION OF THE FIGURES

FIG. 1 shows the DNA sequence of −1354 to +7 of MCK.

DETAILED DESCRIPTION OF THE INVENTION

The present invention is directed to a DNA construct which is useful for immunization or gene therapy. The construct of the invention comprises muscle specific regulatory elements, such as a promoter or a promoter and one or more enhancer elements, and a DNA sequence under control of the muscle specific regulatory elements. The DNA sequence is generally a heterologous sequence, i.e., one which is not natively operably linked to the muscle specific regulatory element. Several DNA sequences may be incorporated into the DNA construct. In one embodiment, the DNA sequence codes for an antigen, antigenic determinant or an epitope of an antigen. In a second embodiment, the DNA sequence is a normal muscle gene which is effected in a muscle disease. In a third embodiment, the DNA sequence is an antisense for blocking an abnormal muscle gene. In a fourth embodiment, the DNA sequence codes for a protein which circulates in the mammalian blood or lymphatic systems. The present invention is useful for ameliorating the effects of diseases of muscle by expression of the normal gene or blocking abnormal gene expression within muscle cells, for the heterologous expression of a transgene which codes for a circulating protein or a protein which modifies a disease state in which muscle is not primarily involved and for vaccine development.

The first element of the DNA constructs of the present invention is a muscle specific regulatory element. A muscle specific regulatory element is any regulatory element which affects the transcription or expression of a gene specifically in muscle tissue and not in other body tissues. The muscle specific regulatory element is generally a muscle specific promoter, but it may also include one or more enhancers. Examples of muscle specific regulatory elements include those which are isolated from muscle specific genes, such as the muscle isozyme of creatine kinase (MCK) (Sternberg et al., 1988), myosin light kinase (Merlie 1992a, 1992b), muscle-specific aldolase (Concordet et al., 1993), muscle-specific enolase (Gaillongo et al., 1993), troponin C (Prigozy et al., 1993), myosin (Kitsis et al., 1991; Takeda et al., 1992, von Harsdorf et al., 1993). Many of these promoters are under the control of the MyoD family of transcription factors (Olsen 1990; Hart 1992). These regulatory elements, as well as other muscle specific regulatory elements, may be modified to remove unnecessary sequences as long as they retain the muscle specificity of action.

The second element of the DNA constructs of the present invention is a DNA sequence which is operably linked to the muscle specific regulatory element. "Operably linked" refers to a juxtaposition wherein the components so described are in a relationship permitting them to function in their intended manner. For instance, a promoter is operably linked to a coding sequence if the promoter affects its transcription or expression. Any DNA sequence which is useful for immunization or gene therapy can be used as the second element of the DNA constructs of the present invention. The DNA sequence is generally a heterologous sequence, i.e., one which is not natively operably linked to the muscle specific regulatory element. In one embodiment, the DNA sequence codes for an antigen, antigenic determinant or an epitope of an antigen. An "antigen" refers to a molecule containing one or more epitopes that will stimulate a host's immune system to make a secretory, humoral and/or cellular antigen-specific response. The term is also used interchangeably with "immunogen."

The DNA sequence will code for the protein portion of the antigen. The host will appropriately modify the protein to its native state in accordance with the signals provided by the protein produced in accordance with the present invention. Thus, the antigen produced in the host antigen can be a protein or a host modified protein. The antigen can be a fusion peptide of two or more antigens. Particularly, the antigen can include a native protein or protein fragment, or a synthetic protein or protein fragment or peptide. The antigen can include glycoprotein, glycopeptide, lipoprotein, lipopeptide, nucleoprotein, nucleopeptide. It can also include a peptide-peptide conjugate. Examples of antigens include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, hemophilus influenza type b, chlamydia, varicella-zoster virus or rabies.

In a second embodiment, the DNA sequence is a normal muscle gene which is effected in a muscle disease. A kinase gene is known to be effected in myotonic dystrophy. In this embodiment, the normal kinase gene would be operably linked to the muscle specific promoter for introduction into muscle. In a third embodiment, the DNA sequence is an antisense for blocking the expression of an abnormal muscle gene. The antisense may bind to the mRNA produced by the muscle gene to prevent translation or it may bind to a regulatory region of the abnormal gene to prevent transcription of the abnormal gene.

In a fourth embodiment, the DNA sequence codes for a protein which circulates in the mammalian blood or lymphatic systems. Examples of circulating proteins include, but are not limited to, insulin, peptide hormones, hemoglobin, growth factors, liver enzymes, clotting factors and enzymes, complement factors, cytokines, tissue necrosis factor and erythropoietin.

The DNA constructs of the present invention can be constructed by a variety of well known methods, and the order of ligation of the parts can be varied. In one embodiment, the DNA constructs are prepared by separately ligating the muscle specific regulatory element and the DNA sequence into any desired vector for immunization or gene therapy or an intermediate vector used in the construction of the vector used for immunization of gene therapy. In a second embodiment, the muscle specific regulatory element and the DNA sequence are ligated together to provide a cassette which can be inserted into any desired vector for immunization or gene therapy. Vectors which can be utilized for immunization and gene therapy include those vectors described above and those generally known in the art. In addition, the DNA construct can be introduced directly into muscle tissue without the use of a vector by techniques known in the art.

The present invention provides a vaccine (or a vaccine composition) comprising the DNA construct and a pharmaceutically acceptable carrier. The DNA construct may be used by itself or it may be incorporated into a vector which is used to make the vaccine. This vaccine is used to immunize mammals, including humans, against a disease by administering to the mammal (human) an effective immunizing amount of the vaccine. An effective immunizing amount of a vaccine is known or can be readily determined by skilled artisans. The vaccine is administered to a subject by injection into muscle tissue. The vaccine induces a continuing protective level of antibody and/or cellular immune response which is directed against the antigen of the DNA construct.

The present invention further provides a therapeutic for ameliorating the effects of diseases of muscle by expression of the normal gene or by blocking abnormal gene expression within muscle cells, or a therapeutic for the heterologous expression of a transgene which codes for a circulating protein or a protein which modifies a disease state in which muscle is not primarily involved. The treatment of a disease is accomplished by introducing the DNA construct of the present invention into muscle tissue. The DNA construct, alone or in a vector, can be introduced directly by injection into muscle tissue. Alternatively, the DNA construct in a vector can be introduced into muscle tissue by any of the know gene therapy techniques discussed above. The DNA construct in a vector can also be introduced into muscle myoblasts in vitro by know techniques and then the treated myoblasts can be returned to an in vivo environment. The DNA construct of the present invention can be used for permanent gene transfer as known in the art. Alternatively, the DNA construct of the present invention can be used for a reversible gene transfer in which the DNA construct does not become integrated into the host's DNA. In reversible gene transfer, the DNA construct is periodically administered much like a pharmaceutical. In this instance the DNA construct is administered when the transcription and expression of the heterologous DNA sequence decreases below a predetermined level.

There are several advantages to the use of regulatory elements (promoters, enhancers and the like) which are selectively expressed in muscle cells. These regulatory elements in a suitable vector offer safety advantages over comparable vectors employing potent constitutive promoters (such as the cytomegalovirus (CMV) promoter). Promoters which require transcription factors specific to differentiated muscle cells will not be active in other cell types. Therefore, should the nucleic acid construct become incorporated into the genome of a non-muscle cell by homologous or non-homologous recombination, it will not cause the constitutive expression of normally silent or regulated genes. The lack of constitutive expression is a distinct advantage over the use of powerful constitutive promoters which could promote the production of undesirable gene products in an unrepressed manner. While the cloned nucleotide sequence being driven by the muscle specific regulatory elements will be constitutively expressed in muscle cells, recombination leading to insertion of the vector in these cells will be less likely to lead to deleterious events, disrupt normal cell function or homeostasis. This advantage is principally due to the multi-nucleated nature of myotubes. Integration via homologous recombination will only knock out one of multiple copies of the gene from which the muscle specific regulatory elements were derived, and the effects of a nonhomologous recombination could be diluted by alleles present in other unaffected nuclei.

The present invention is described by reference to the following Examples, which are offered by way of illustration and are not intended to limit the invention in any manner. Standard techniques well known in the art or the techniques specifically described below were utilized. For illustration purposes, the examples utilize the regulatory elements of MCK and the glycoprotein D2 gene of Herpes simplex virus type 2. However, any of the regulatory elements mentioned above or other muscle specific regulatory elements could be used in place of the MCK regulatory elements and other DNA sequences can be used in place of the glycoprotein D2 gene.

EXAMPLE 1

Isolation of the MCK Promoter

The mouse MCK gene promoter and enhancer elements isolated in accordance with this example correspond to nucleotides −1354 to +7 of the mouse MCK gene (Sternberg et al., 1988) and is set forth in FIG. 1 and SEQ ID NO: 1. The MCK gene promoter and enhancer was isolated from mouse genomic DNA by PCR using conventional techniques and manufacturer's recommended procedures. The PWO polymerase was utilized to limit potential errors in the amplification of the MCK gene elements. The following primers were utilized:

forward: 5'-GA AGATCTCAGCTGAGGTGCAAAAGGCTCCTG-3' (SEQ ID NO:2) and reverse: 5'-CCC AAGCTTGTGACCCGGGGGCAGCCCCTGTGCC-3' (SEQ ID NO:3).

The nucleotides underlined in the forward primer indicate a Bgl II site, and the nucleotides underlined in the reverse primer indicate a Hind III site.

Figure 2:
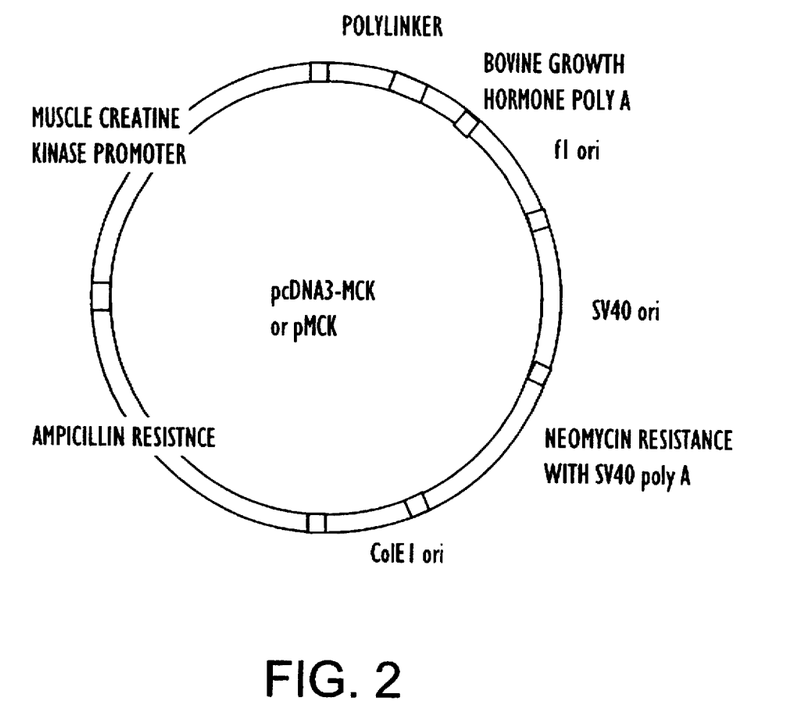
FIG. 2 shows a map of pMCK.
Figure 3:
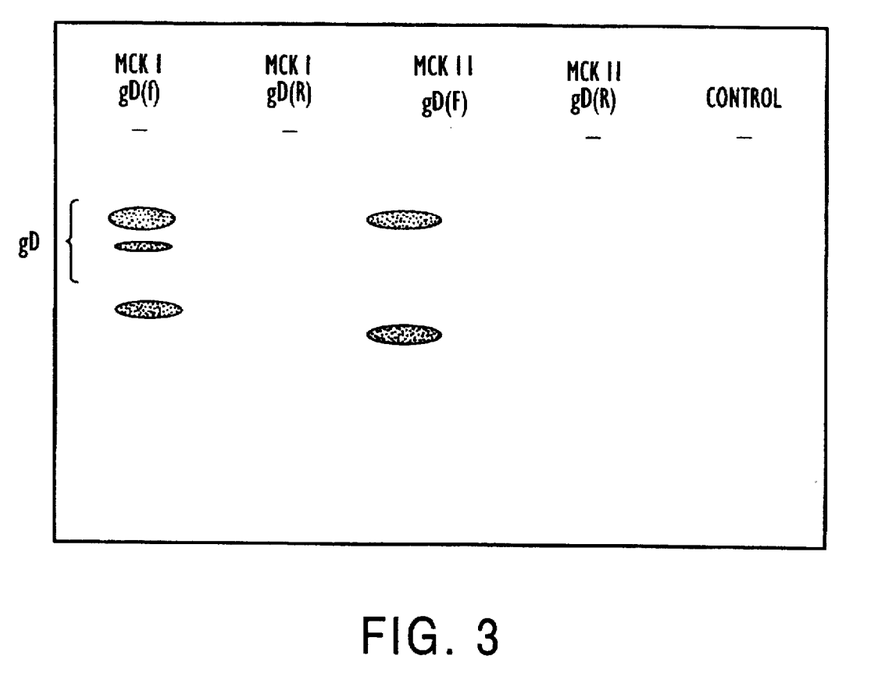
FIG. 3 shows a representation of a Western blot demonstrating production of Herpes simplex virus glycoprotein gD2 in transfected muscle cells.

The plasmid pCDNA3 was obtained from Invitrogen (San Diego, Calif.). This plasmid contains a cytomegalovirus (CMV) promoter with a polylinker downstream of the promoter. The CMV promoter was removed from pCDNA3 by digestions with Hind III and Bgl II. The amplified MCK gene was digested with Hind II and Bg1 II and inserted into the digested pCDNA3 to produce pMCK. A map of pMCK is shown in FIG. 2.

EXAMPLE 2

Insertion of gD2 Gene of Herpes Simplex Type 2 in pMCK

The plasmid pWW65 (Muggeridge et al., 1990) was obtained from Gary Cohen and Roselyn Rosenberg of the University of Pennsylvania (Philadelphia, Pa.). This plasmid contains the Herpes simples virus glycoprotein D2 (gD2) gene with Hind III linkers which was inserted into the Hind III site of pRSVnt EPA under control of the Rous sarcoma virus long terminal repeat promoter. The gD2 gene was isolated from pWW65 by digestion with Hind III and inserted into the Hind III site of pMCK downstream of the MCK regulatory elements. Two plasmids were isolated, pMCKgDf, in which the gD gene was inserted in the correct orientation, and pMCKgDr, in which the gD gene was inserted in the reverse orientation.

EXAMPLE 3

In Vitro Production of gD2 in Muscle Cells

The C2C12 muscle cell line was transfected by conventional techniques with either the pMCKgDf or pMCKgDr, the latter acting as the control. In addition, to test for the specificity of the construct, Cos cells were transfected by conventional techniques with either pMCKgDf or pMCKgDr. Cos cells were chosen to be biased against the muscle specificity of the vector, since the vector can be amplified in Cos cells due to the combination of SV40 T antigen expression by the cells ant the presence of an SV40 origin of replication in the vector. This amplification would lead to a larger number of vectors per Cos cell that per C2C12 cell and hence a greater chance for gene expression. The transfected cells were grown and the expression of gD was monitored by western blot analysis. The results are shown in FIG. 4. This figure shows that C2C12 cells transfected with pMCKgDf produced immunogenic gD, whereas C2C12 cells transfected with pMCKgDr did not produce immunogenic gD. Cos cells transfected with either pMCKgDf or pMCKgDr did not produce detectable amounts of gD.

EXAMPLE 4

In Vivo Production of gD in Muscle Tissue and Generation of an Immune Response Six to eight week old female BALB/c were used for this example. The mice were divided into three groups and immunized with 100 μg of either pMCKgDf, pMCKgDr or pRSVnt three times at weekly intervals. The pMCKgDr acted as a first control and the pRSVnt acted as a second control. Prior to viral challenge, the mice were pretreated subcutaneously with 2.0 mg of medroxyprogesterone to induce uniform susceptibility to viral challenge (Teepe et al., 1990). An intravaginal live viral challenge with $5.3\times10^4$ to $1.7\times10^5$ PFU/ml HSV-2 MS strain adsorbed to Dacron pledgets was performed two to three weeks after the last vaccination. Vaginal washing viral titres were obtained by plaque assay of vaginal washing specimens. Viral titres were compared using the Mann-Whitney U test. Mice were scored daily for development of genital disease. Severe disease was defined as:

- the presence of genital maceration on two consecutive days;
- the development of urinary retention;
- the development of profound cachexia; or
- the development of hindlimb paralysis.

Serology assays for antibody titres and neutralizing antibodies were conducted using conventional techniques. ELISA was conducted by coating ninety-six well plates with 3 μg of baculovirus expressed gD2. Non-specific binding was prevented by incubating ELISA plates with a solution of normal goat serum, Tween and saline. Samples were diluted serially 1:2 staring at 1:1000. Binding of anti |gD2 antibodies was detected by incubation with peroxidase tagged goat-anti-mouse IgG antibodies. ELISA units were obtained by regression analysis of log-transformed optical densities. Serum anti-gD2 antibody titres (by ELISA) and neutralizing activities were compared using the Mann-Whitney U test.

Figure 4:
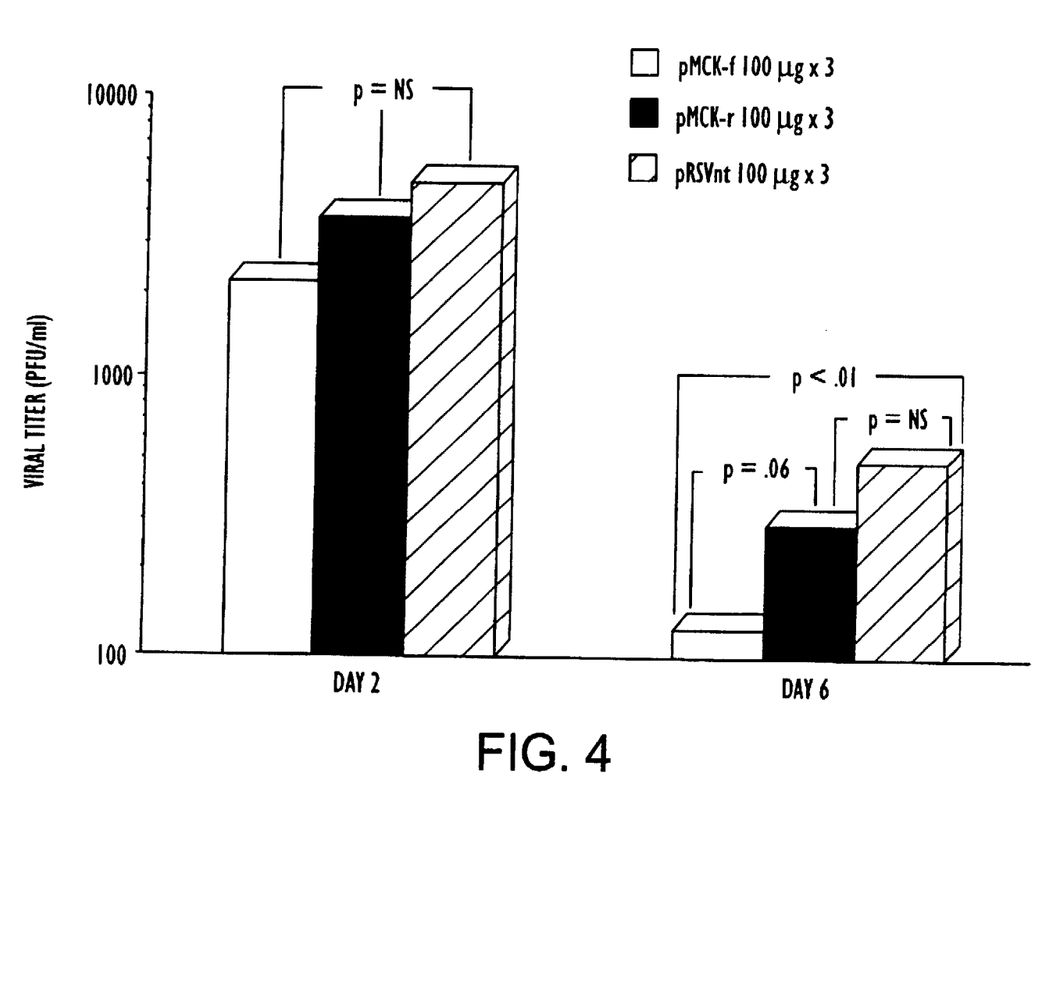
FIG. 4 shows the geometric mean viral titres post-challenge in vaginal washings of mice immunized with the pMCKgDf or control plasmids.

FIG. 4 shows the geometric mean viral titres post-challenge in vaginal washings from the immunized mice. The viral titres were similar in the three groups of mice two days post-challenge. The viral titres were decreased in the pMCKgDf immunized mice six days post-challenge compared to pMCKgDr or pRSVnt immunized mice (geometric mean titres 126, 288 489 PFU/ml. respectively; $p<0.05$).

Figure 5:
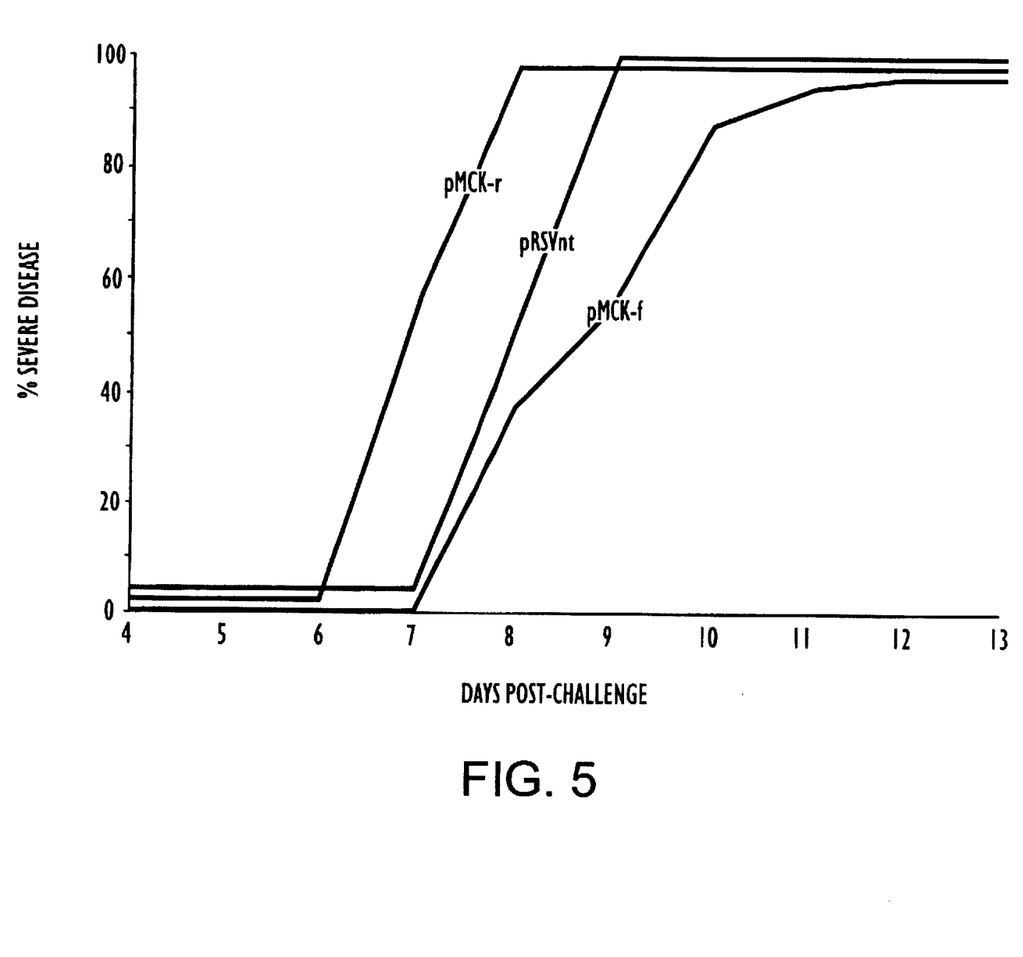
FIG. 5 shows the development of severe clinical disease among mice immunized with pMCKgDf or control plasmids.

FIG. 5 shows the development of severe disease in the immunized mice following challenge. Development of severe disease was markedly delayed among the pMCKgDf immunized mice compared to the pMCKgDr or pRSVnt immunized mice (median 9, 7, 7 days, respectively; $p <0.01$).

EXAMPLE 5

In Vivo Production of gD in Muscle Tissue and Generation of an Immune Response Example 4 was repeated in which 0.1 µg of 1,25-dihydroxy Vitamin $D_3$ (1,25$(OH)_2D_3$) was used as an adjuvant for the immunizations. The use of 1,25$(OH)_2D_3$ as an adjuvant resulted in an enhanced reduction of viral titres as measured in the vaginal washings and further resulted in enhanced serum antibody titres as measured by ELISA and enhanced serum neutralizing antibodies.

EXAMPLE 6

Dose Effects of pMCKgD Immunization

Six to eight week old female BALB/c were divided into five groups and immunized with varying doses (3 µg, 10 µg, 30 µg or 100 µg) of pMCKgDf or 100 µg pMCKgDr three times at weekly intervals. The immunizations were made using 0.1 µg of (1,25$(OH)_2D_3$) as an adjuvant. The mice were treated and challenged with HSV as described in Example 4. The severity of disease and serology assays were analyzed as described in Example 4.

Figure 6:
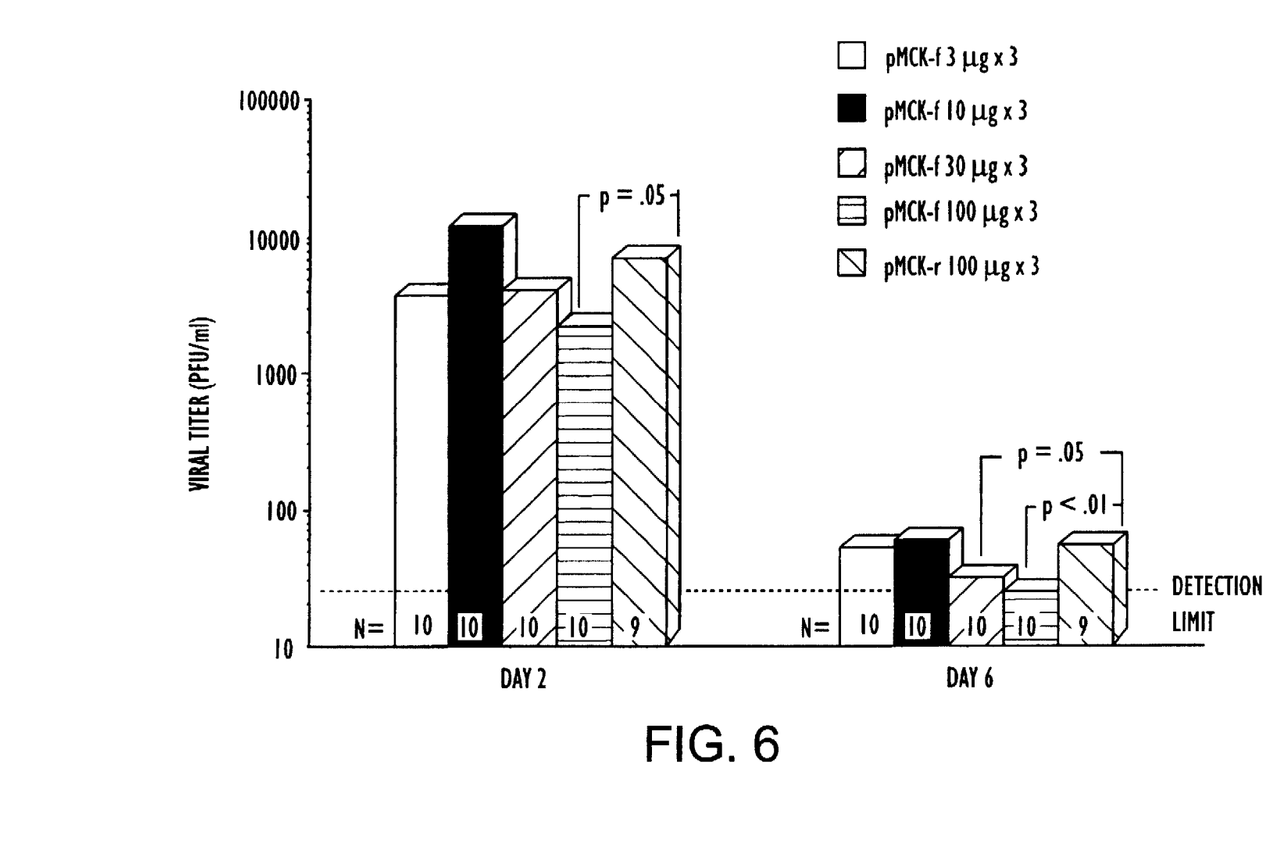
FIG. 6 shows the geometric mean viral titres post-challenge in vaginal washings of mice immunized with varying doses of pMCKgDf.

FIG. 6 shows the geometric mean viral titres post-challenge in vaginal washings from the immunized mice. This figure shows dose related effects on the viral titres in vaginal washings. FIG. 6 shows that the viral titre for the 100 µg pMCKgDf immunized mice was significantly lower ($p=0.05$) than the viral titre for the control pMCKgDr immunized mice at two days post challenge. FIG. 6 shows that at six days post challenge, the viral titres for the 30 µg and 100 µg pMCKgDf immunized mice were significantly lower than the viral titre for the control pMCKgDr ($p=0.05$, $p<0.01$, respectively.

Figure 7:
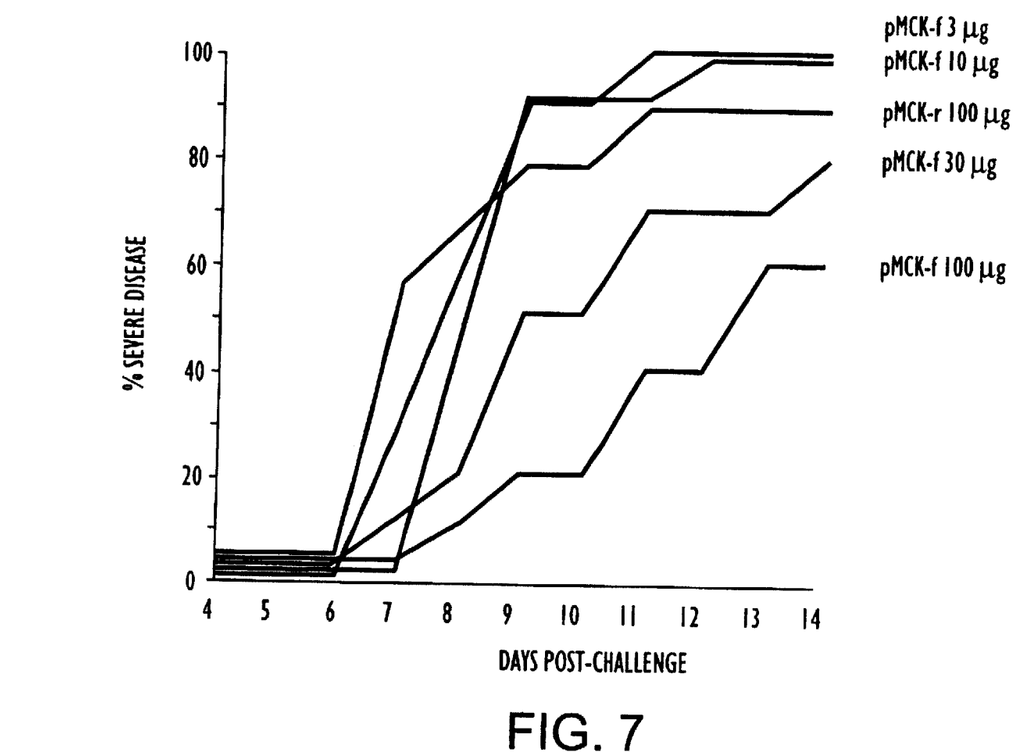
FIG. 7 shows the development of severe clinical disease among mice immunized with varying doses of pMCKgDf.

FIG. 7 shows the development of severe disease in the immunized mice following challenge. This figure shows dose related effects on the development of severe clinical disease. Development of severe disease was markedly delayed among the pMCKgDf immunized mice compared to the pMCKgDr immunized mice ($p=0.02$).

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Anderson, et al. (1980). Proc. Natl. Acad. Sci. USA 77:5399–5403.
Ascadi, G. et al. (1991). Nature 352:815.
Berkner (1992). Curr. Top. Microbiol. Immunol. 158:39–61.
Berkner, et al. (1988). BioTechniques 6:616–629.
Brandyopadhyay and Temin (1984). Mol. Cell. Biol. 4:749–754.
Breakfield and Geller (1987). Mol. Neurobiol. 1:337–371.
Brinster, et al. (1981). Cell 27:223–231.
Buchschacher and Panganiban (1992). J Virol. 66:2731–2739.
Buskin, J. et al. (1989). Mol. Cell Biol. 9:2627–2640.
Chamberlain, J. S. et al. (1985) Mol. Cell Biol. 5:484–492.
Collins, D. et al. (1992). J Immunol. 148:3335.
Concordet, J. et al. (1993). Mol. Cell. Biol. 13:9.
Constantini and Lacy (1981). Nature 294:92–94.
Cooney, E. et al. (1991). Lancet 337:567.
Cotten, et al. (1990). Proc. Natl. Acad. Sci. USA 87:4033–4037.
Culver, et al. (1992). Science 256:1550–1552.
Curiel, et al. (1991 a). Proc. Natl. Acad. Sci. USA 88:8850–8854.
Curiel, et al. (1991 b). Hum. Gene Ther. 3:147–154.
Eglitis, M. and Anderson, W.F. (1988). Biotechniques 6:608.
Eppenberger, H. M. et al. (1964). Dev. Biol. 10:1–16.
Fazio, V. M., et al. (1994). Biochem. Biophys. Res. Comm. 200:298.
Felgner, et al. (1987). Proc. Nail. Acad Sci. USA 84:7413–7417.
Fink, et al. (1992). Hum. Gene Ther. 3:11–19.
Freese, et al. (1990). Biochem. Pharmacol. 40:2189–2199.
Friedmann, T. (1989). Science 244:1275.
Gaillongo, A. et al. (1993). Eur. J. Biochem. 214:367.
Gammelin et al. (1989). Virology 70:71.
Germain, R. (1981). Nature 353:605.
Gordon, et al. (1980). Proc. Natl. Acad. Sci. USA 77:7380–7384.
Gorman et al. (1991). J Virol. 65:3704.
Gorziglia and Kapikian (1992). J. Virol. 66:4407–4412.
Graham and van der Eb (1973). Virology 52:456–467.
Hahn, C. et al. (1992). Proc. Nat. Acad. Sci. USA 89:2679.
Hart, S. (1992). BioScience 42:582.
Helseth, et al. (1990). J Virol. 64:2416–2420.
Hock, L. J. et al. (1993). U.S. Patent No. 5,273,876.
Jaynes, J. B. et al. (1986). Mol. Cell Biol. 6:2855–2864.
Jaynes, J. B. et al. (1988). Mol. Cell Biol. 8:62–70.
Jockers-Wretou, E. et al. (1975). Clin. Chem. Acta. 50:233–232.
Johnson, et al. (1992). J. Virol. 66:2952–2965.
Kaneda, et al. (1989). J Biol. Chem. 264:12126–12129.
Kieny, M-P. et al. (1992). U.S. Patent No. 5,169,763.
Kitsis, R. et al. (1991). Proc. Nat. Acad. Sci. USA 88:4138.
Klein, T. M., et al. (1987). Nature 327:70.
Ledley, F. D. (1987). J: Pediatrics 110:1.
Lim, et al. (1992). Circulation 83:2007–2011.
Madzak, et al. (1992). J Gen. Virol. 73:1533–1536.
Mann and Baltimore (1985). J. Virol. 54:401–407.
Margolskee (1992). Curr. Top. Microbiol. Immunol. 158:67–90.
Mascola, L. et al. (1989). Arch. Intern. Med 149:1569.
Merlie, J. (1 992a). Cell 69:67.
Merlie, J. (1 992b). Cell 69:79.
Miller, A. (1992). Curr. Top. Microbiol. Immunol. 158:1.
Miller, et al. (1985). Mol. Cell. Biol. 5:431–437.
Miller, et al. (1988). J. Virol. 62:4337–4345.
Moss (1992). Curr. Top. Microbiol. Immunol. 158:25–38.

Muzyczka (1992). *Curr. Top. Microbiol. Immunol.* 158:97–123.
Nabel, et al. (1990). *Science* 249:1285–1288.
Nabel (1992). *Hum. Gene Ther.* 3:399–410.
Nabel, G. J., et al. (1993). *Proc. Natl. Acad. Sci. USA* 87:11307.
Ohi, et al. (1990). *Gene* 89:279–282.
Olsen, E. (1990). *Genes and Development* 4:1454.
Page, et al. (1990). *J. Virol.* 64:5370–5276.
Pellicer, et al. (1980). *Science* 209:1414–1422.
Perriard, J. C. (1979). *J Biol. Chem.* 254:7036–7041.
Perriard, J. C. et al. (1978). *Arch. Biochem. Biophys.* 191:90–100.
Petropoulos, et al. (1992). *J Virol.* 66:3391–3397.
Prigozy, T. et al. (1993). *Somatic Cell Mol. Genet.* 19:111.
Quantin, et al. (1992). *Proc. Natl. Acad. Sci. USA* 89:2581–2584.
Richterich, R. et al. (1967). Comparative studies on creatine kinase and its isoenzymes, pp. 243–253. In: N van Thoai et al. (eds.), *Homologous Enzymes and Biochemical Evolution*, Gordon and Breach Publishers, New York, N.Y.
Rosenberg, U. B. et al. (1982). *Proc. Nat. Acad. Sci. USA* 79:6589–6592.
Rosenfeld, et al. (1992). *Cell* 68:143–155.
Shimada, et al. (1991). *J Clin. Invest.* 88:1043–1047.
Sorge, et al. (1984). *Mol. Cell. Biol.* 4:1730–1737.
Srivastava, A. (1993). U.S. Patent No. 5,242,479.
Sternberg, E. A., et al. (1988). *Mol. Cell. Biol.* 8:2896.
Stewart, et al. (1992). *Hum. Gene Ther.* 3:267–275.
Stratford-Perricaudet, et al. (1990). *Hum. Gene Ther.* 1:241–256.
Takeda, S. et al. (1992). *J Biol. Chem.* 267:16957.
Tanzer, M. L. et al. (1959). *J Biol. Chem.* 234:3201–3204.
Taylor, P. et al. (1986). *Immunology* 58:417.
Teepe, A. G. et al. (1990). *Antiviral Res.* 14:227.
Townsend, A. et al. (1989). *Ann. Rev. Immunol.* 7:601.
von Harsdorf, R. et al. (1993). *Circulat. Res.* 72:689.
Wagner, et al. (1990). *Proc. Natl. Acad. Sci. USA* 87:3410–3414.
Wagner, et al. (1991). *Proc. Natl. Acad Sci. USA* 88:4255–4259.
Wang and Huang (1989). *Biochemistry* 28:9508–9514.
Wilkinson, et al. (1992). *Nucleic Acids Res.* 20:2233–2239.
Wolff, J. A., et al. (1990). *Science* 247:1465 (1990).
Wolff, J. A., et al. (1991). *BioTechniques* 11:474–485.
Wolff, J. et al. (1992). *Hum. Mol. Genet.* 1:363.
Wooster, R., et al. (1994). *Science* 265:2088.
Wu, et al. (1989a). *Genomics* 4:560–569.
Wu, et al. (1989b). *J Biol. Chem.* 264:16985–16987.
Wu, et. al. (1991). *J Biol. Chem.* 266:14338–14342.
Yang, N. S., et al. (1990). *Proc. Natl. Acad. Sci. USA* 87:9568.
Yankauckas, M. A., et al. (1993). *DNA Cell Biol.* 12:771.
Yewdell, J. et al. (1989). *Science* 244:1072.
Zenke, et al. (1990). *Proc. Natl. Acad. Sci. USA* 87:3655–3659.

---

What is claimed is:

1. A vaccine DNA construct for the expression of a heterologous DNA sequence in muscle tissue comprising a muscle specific regulatory element of muscle isozyme of creatine kinase (MCK) having the nucleotide sequence set forth in SEQ ID NO:1 and a heterologous DNA sequence operably linked to said element, wherein said heterologous DNA sequence codes for an antigen, an antigenic determinant or an epitope of an antigen and is expressed when said DNA construct is introduced into muscle tissue.

2. The DNA construct of claim 1, wherein said antigen is selected from the group consisting of viral or bacterial hepatitis, influenza, diphtheria, tetanus, pertussis, measles, mumps, rubella, polio, pneumococcus, herpes, respiratory syncytial virus, hemophilus influenza type b, chlamydia, varicella-zoster virus or rabies.

3. A vector which comprises the DNA construct of claim 1.

4. The vector of claim 3 further comprising a nucleotide sequence capable of integration into a host chromosome.

5. The vector of claim 3 further comprising a nucleotide sequence capable of replication in a host.

6. A vector which comprises the DNA construct of claim 2.

7. The vector of claim 6 further comprising nucleotide sequence capable of integration into a host chromosome.

8. The vector of claim 6 further comprising a nucleotide sequence capable of replication in a host.

9. A vaccine comprising the DNA construct of claim 1 and a physiologically acceptable carrier.

10. A vaccine comprising the DNA construct of claim 2 and a physiologically acceptable carrier.

11. A vaccine comprising the vector of claim 3 and a physiologically acceptable carrier.

12. A vaccine comprising the vector of claim 4 and a physiologically acceptable carrier.

13. A vaccine comprising the vector of claim 5 and a physiologically acceptable carrier.

14. A vaccine comprising the vector of claim 6 and a physiologically acceptable carrier.

15. A vaccine comprising the vector of claim 7 and a physiologically acceptable carrier.

16. A vaccine comprising the vector of claim 8 and a physiologically acceptable carrier.

\* \* \* \* \*